United States Patent
Diener et al.

(12) 
(10) Patent No.: US 6,299,770 B1
(45) Date of Patent: Oct. 9, 2001

(54) PORTABLE ULTRAVIOLET WATER DISINFECTION DEVICE

(76) Inventors: Ray R. Diener; Thomas R. Hecht, both of 1016 W. Ridge Rd, Elizabethtown, PA (US) 17022

( * ) Notice: Subject to any disclaimer, the term of this patent is extended or adjusted under 35 U.S.C. 154(b) by 0 days.

(21) Appl. No.: 09/621,837

(22) Filed: Jul. 24, 2000

(51) Int. Cl.[7] ................... C02F 1/32; B01J 19/08
(52) U.S. Cl. ............ 210/252; 210/266; 210/748; 210/917; 422/186.3
(58) Field of Search ................ 210/266, 252, 210/259, 464, 748, 916, 917; 422/24, 186.3; 250/436

(56) References Cited

U.S. PATENT DOCUMENTS

| | | |
|---|---|---|
| 3,965,008 | 6/1976 | Dawson . |
| 4,008,045 * | 2/1977 | Free . |
| 4,066,551 | 1/1978 | Stern . |
| 4,089,768 | 5/1978 | Fischer et al. . |
| 4,101,777 * | 7/1978 | Reid . |
| 4,615,799 | 10/1986 | Mortenson . |
| 4,755,292 * | 7/1988 | Merriam . |
| 4,857,204 * | 8/1989 | Joklik . |
| 4,956,754 | 9/1990 | Chen . |
| 5,026,477 | 6/1991 | Yen . |
| 5,106,495 * | 4/1992 | Hughes . |
| 5,401,394 | 3/1995 | Markham . |
| 5,536,395 | 7/1996 | Kuennan et al. . |
| 5,785,845 * | 7/1998 | Colaiano . |
| 5,853,676 * | 12/1998 | Morgan, Jr. . |
| 5,916,439 | 6/1999 | Oleskow . |
| 6,110,424 * | 8/2000 | Maiden et al. . |
| 6,180,003 * | 1/2001 | Reber et al. . |
| 6,245,229 * | 6/2001 | Kool et al. . |

* cited by examiner

*Primary Examiner*—David A. Simmons
*Assistant Examiner*—Fred Prince
(74) *Attorney, Agent, or Firm*—John D. Gugliotta

(57) ABSTRACT

A water disinfection device is provided having a base for a stabilized support. The base forms a support collar having an annular retaining ring held by a retaining arm, and which holds a durable container of a volume not to exceed 2 liters. A disinfection module provides an ultraviolet disinfection source such that the distance between the surface of the disinfection module and the interior of the durable container is less than 7.5 centimeters at any point except the opening.

11 Claims, 5 Drawing Sheets

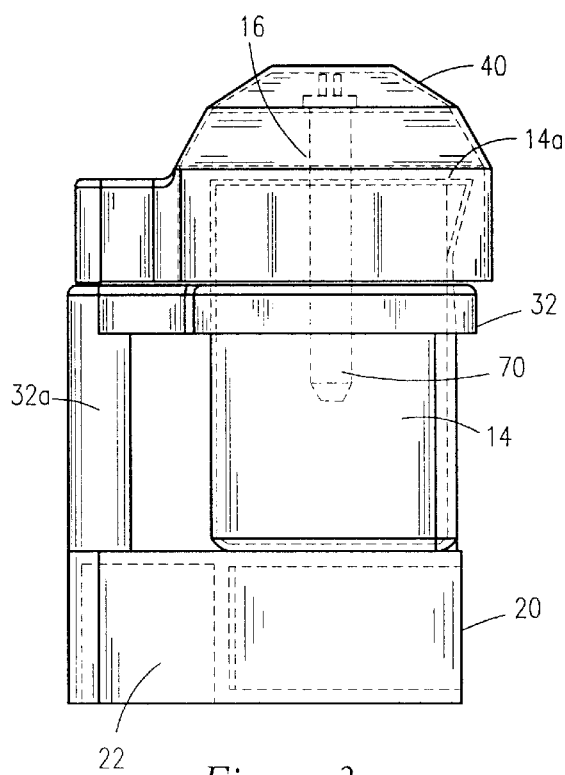
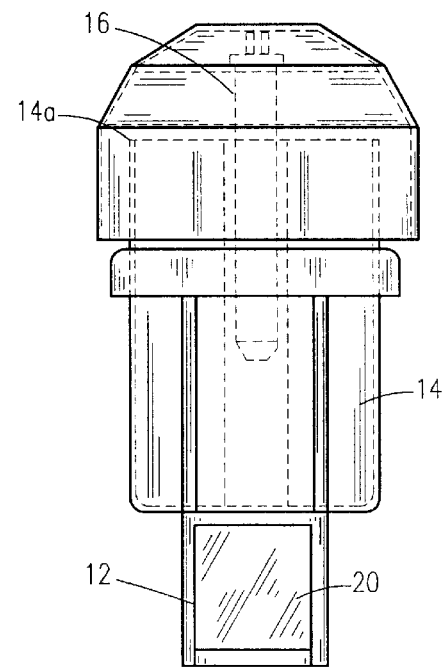
Figure 3
Figure 4

PORTABLE ULTRAVIOLET WATER DISINFECTION DEVICE

RELATED APPLICATIONS

The present invention was first described in Disclosure Document No. 466,946, filed on Jan. 10, 2000. There are no previously filed, nor currently any co-pending applications, anywhere in the world.

BACKGROUND OF THE INVENTION

1. Field of the Invention

The present invention relates generally to devices which utilize ultraviolet radiation and, more particularly, to a portable fluid container with an integral ultraviolet lighting system powered by direct current.

2. Description of the Related Art

One of the most basic necessities for human life is water. While large scale filtering and purification plants do a superb job of keeping a supply of fresh, clean water to most humans, there are times when such access is not handy. These times occur while camping, hunting, fishing and during other outdoor activities at remote conditions. They also occur while traveling to locations where water quality is questionable such as overseas locations. While such methods as portable filters and iodine tablets do exist to help in the filtering process, some bacteria and germs are still present. Ultraviolet light has proven to be an effective disinfection method for such bacteria and germs but such ultraviolet systems require connection to the AC power grid and are not suitable for remote locations.

A search of the prior art did not disclose any patents that read directly on the claims of the instant invention; however, the following references were considered related.

The following patents an ultraviolet radiation for disinfecting potable water.

U.S. Pat. No. 5,916,439 issued in the name of Oleskow

U.S. Pat. No. 5,536,395 issued in the name of Kuennan et al.

U.S. Pat. No. 5,026,477 issued in the name of Yen

U.S. Pat. No. 4,615,799 issued in the name of Mortenson

The following patents describe a portable water disinfecting device.

U.S. Pat. No. 4,066,551 issued in the name of Stern

U.S. Pat. No. 3,965,008 issued in the name of Dawson

U.S. Pat. No. 5,401,394 issued in the name of Markham discloses a water treatment system ultraviolet bulb voltage monitor circuit.

U.S. Pat. No. 4,956,754 issued in the name of Chen describes an ultraviolet lamp assembly for destroying microorganisms in aquarium water.

U.S. Pat. No. 4,089,768 issued in the name of Fischer et al. discloses a battery-operated water purification system.

Consequently, a need exists for a means by which water can be disinfected by ultraviolet light without connection to an AC power source.

SUMMARY OF THE INVENTION

Therefore, it is an object of the invention to provide for a portable water treatment apparatus capable of disinfecting the liquid contents held therein.

Briefly described according to one embodiment of the present invention, a portable ultraviolet water disinfecting device is provided as a portable apparatus that disinfects water using ultraviolet light. The main housing of the invention is a two liter durable container with an opening at top. Filtered water is charged into this opening until the container is filled to a predetermined recommended fillpoint. An ultraviolet lamp is then inserted into the opening. A ballast powered by a DC source (such as a rechargeable battery) allows for the operation of the light without connection to an AC power grid. After an appropriate period of time, the water inside will be disinfected of any bacteria or germs that can be killed by ultraviolet light. The invention also includes a power inlet for connection to an external DC source (such as a cigarette lighter) to operate the invention or recharge the DC source. It is envisioned that the invention would be suited for use while camping and is especially suited for use during travel to overseas locations where water quality is questionable.

The use of the present invention allows for the disinfection of water by ultraviolet light in a quick, easy and effective manner at any location without reliance on external sources of power.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 3 is a side elevational view thereof;

FIG. 4 is a front elevational view thereof;

DESCRIPTION OF THE PREFERRED EMBODIMENTS

1. Detailed Description of the Figures

Figure 1:
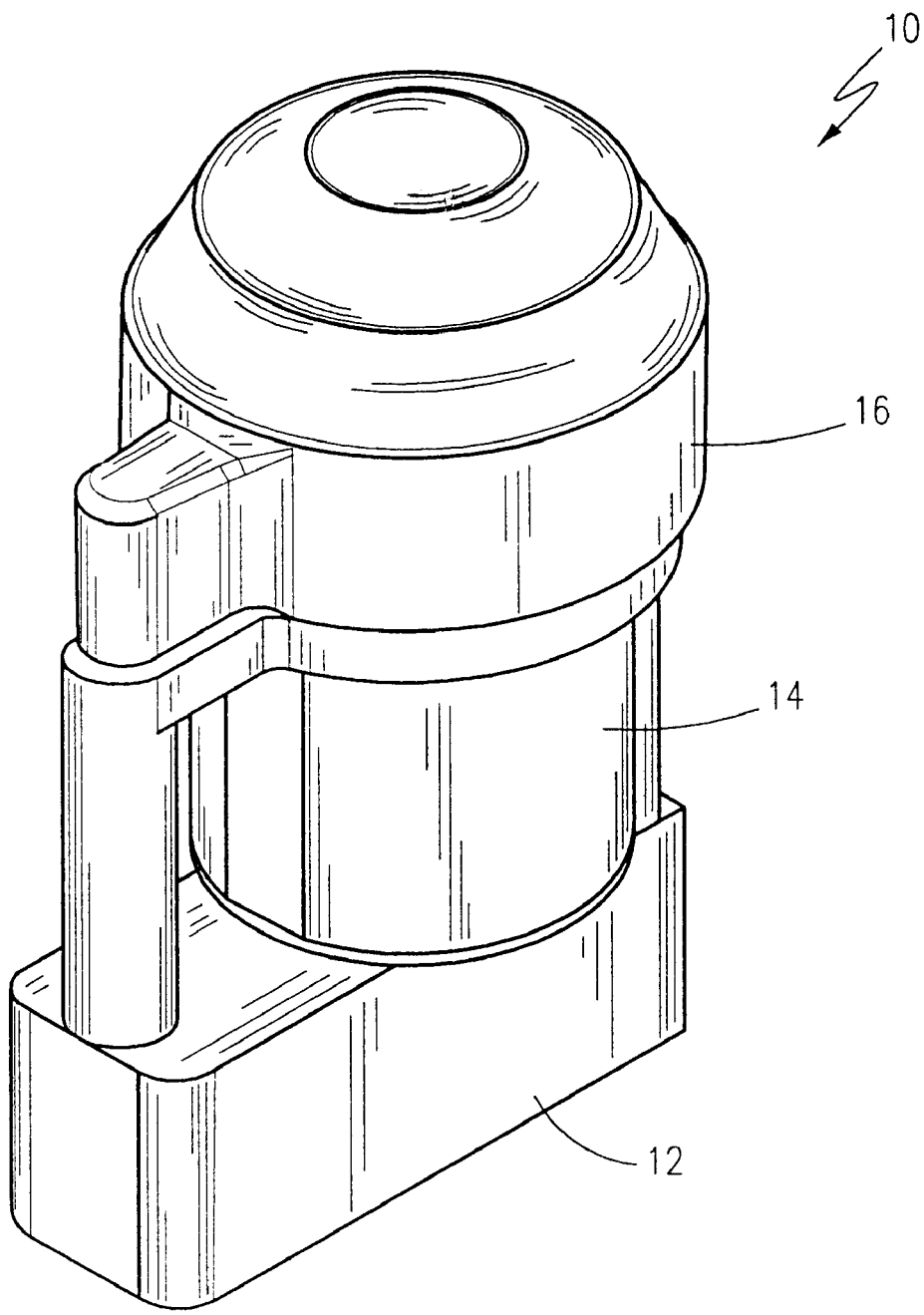
FIG. 1 is a perspective view of a portable ultraviolet water disinfection device according to the preferred embodiment of the present invention.
Figure 2:
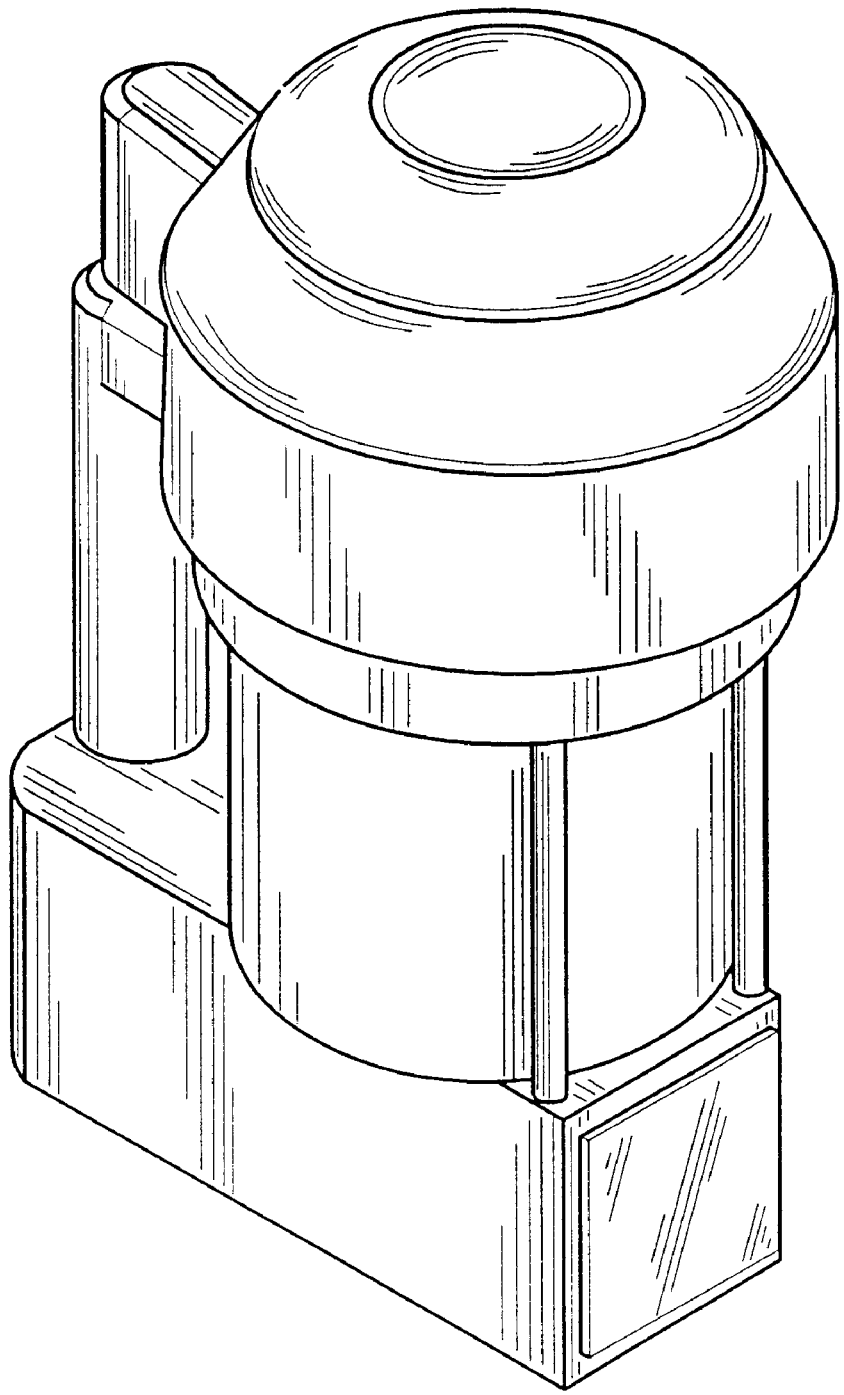
FIG. 2 is a reverse perspective view thereof.
Figure 5:
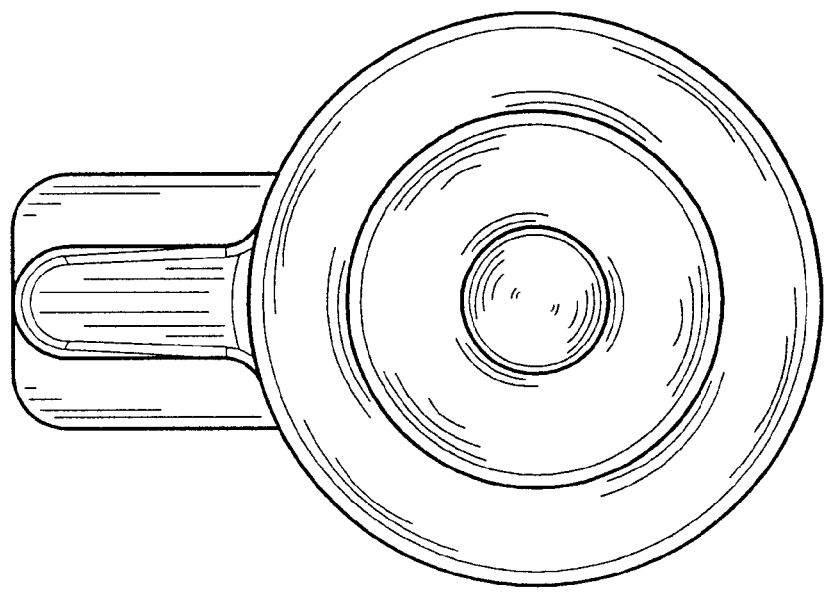
FIG. 5 is a top plan view thereof.
Figure 6:
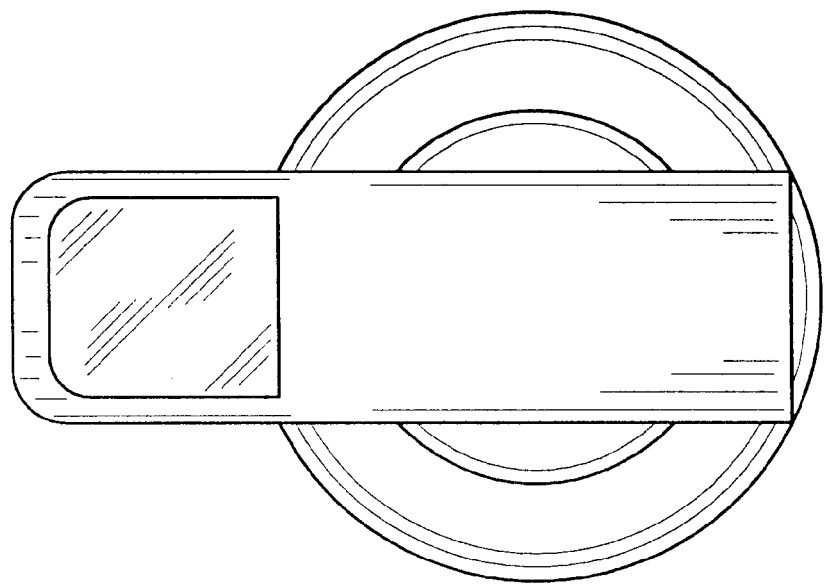
FIG. 6 is a bottom plan view thereof.
Figure 7:
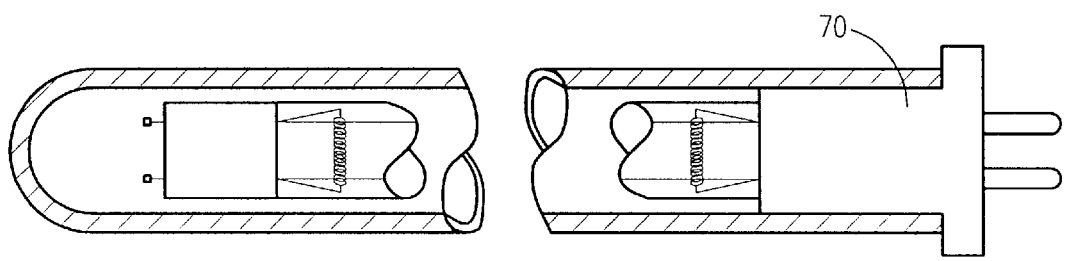
FIG. 7 is a schematic representation of an ultraviolet lamp assembly for use with the present invention.

Referring now to FIGS. 1–6, a portable ultraviolet water disinfection device, generally noted as 10, is provided as a portable apparatus that disinfects water using ultraviolet light. The main housing of the device comprises three main components; a base 12 for support, a 2 liter (maximum) durable container 14 that functions as a water treatment canister and final dispensing unit; and, a disinfection module 16.

In greater detail, the base 12 functions as a stabilized support for the device 10, and further provides a housing for a direct current power source, such as a battery 20. Further, the base 12 houses a ballast 22 which powers the ultraviolet source 70. It is anticipated that the present invention will be utilized in a portable, in-situ fashion. It is also therefore anticipated that pre-filtration of the water supply may be required in order to remove particulate and color bodies. A pump or gravity filters in the 0.5–3.0 micron range and containing activated carbon will improve the clarity, taste, and odor of the water and assure proper ultraviolet disinfection. Further, the base 12 forms a support collar 32 held by a retaining arm 32a for retaining the container 14 is a firm fashion centered on the base.

Finally, the disinfection module 16 is described in greater detail. A dome shaped upper housing 40 supports an ultraviolet disinfection source 70 vertically downward at the vertical, radial center of the upper housing 40.

Although generally available commercially are a number of standard ultraviolet lamp elements that can be utilized as an ultraviolet disinfection source 70, it is a primary teaching of the present invention to provide a portable, fully integrated system that allows for reliable water disinfection in a consistent, repeatable fashion. To accomplish this, it is felt that standardization of components, dimensions, and method of disinfection are important. In particular, a standardized ultraviolet lamp element positioned in a known, repeatable fashion is used. By way of disclosure of the known best mode, and not by way of limitation, a lamp type GPH127T5L as manufactured by First Light Technologies, Inc., or functional equivalent, is utilized to provide a sterilizing ultraviolet light source. In order to accommodate portable operation, a direct current power source, such as a rechargeable battery, is housed within the base and is in controlled electronic communication with the lamp 70 through the appropriate regulating ballast 22. Alternately, a power inlet for connection to an external DC source (such as a cigarette lighter on a motor vehicle) to operate the invention and charge the battery.

2. Operation of the Preferred Embodiment

In operation of the present invention, filtered water is poured into the opening of the durable container to the recommended, predetermined fillpoint. An ultraviolet lamp is then inserted into the opening 14. A ballast and a rechargeable battery then allows for the operation of the light without connection to an AC power grid.

In order to operate effectively, there are a number of parameters that must be met in conjunction with the above described design. For example, the distance between the surface of the ultraviolet bulb 70 and the interior of the durable container 14 is required to be less than 7.5 centimeters at any point except the opening. Also, the ultraviolet source must not be completely below the opening 14a of the durable container 14, but rather above, and not exceeding ⅜ inch, for the purpose of disinfecting the opening 14a itself as well as the surrounding surfaces. Further performance is provided with the interior of the durable container 14 having a reflective means, as well as the interior of the dome having a reflective means.

After an appropriate period of time, the water inside will be disinfected of any bacteria or germs that can be killed by ultraviolet light. It is envisioned that the invention would be suited for use while camping and is especially suited for use during travel to overseas locations where water quality is questionable. As such, the period of time required for disinfection of the water may vary with small amounts of turbidity, which may be regulated by measuring water clarity with a turbidity sensor which controls the electronic timer, or alternately functions as an interlock to disallow continued operation.

As designed, a device embodying the teachings of the present invention is easily applied. The foregoing description is included to illustrate the operation of the preferred embodiment and is not meant to limit the scope of the invention. As one can envision, an individual skilled in the relevant art, in conjunction with the present teachings, would be capable of incorporating many minor modifications that are anticipated within this disclosure. Therefore, the scope of the invention is to be broadly limited only by the following claims.

What is claimed is:

1. A water disinfection device comprising:
   a base for functioning as a stabilized support, said base forming a support collar having an annular retaining ring held by a retaining arm;
   a durable container of a volume not to exceed 2 liters, said durable container for functioning as a water treatment canister and final dispensing unit, said durable container being retained in a firm fashion centered on said base by said annular retaining ring; and
   a disinfection module;
   and wherein said water disinfection device can be utilized in a portable, in-situ fashion.

2. The water disinfection device of claim 1, wherein said base further provides a housing for a direct current power source and houses a ballast which powers said disinfection module.

3. The water disinfection device of claim 1, wherein said disinfection module comprises an ultraviolet source.

4. The water disinfection device of claim 1, further comprising pre-filtration means for pre-filtering of the water supply in order to remove particulate and color bodies.

5. The water disinfection device of claim 4, wherein said pre-filtration means comprises filters in the 0.5–3.0 micron range and containing activated carbon.

6. The water disinfection device of claim 1, wherein said disinfection module comprises a dome shaped upper housing supporting an ultraviolet disinfection source vertically downward at the vertical, radial center of the upper housing.

7. The water disinfection device of claim 6, wherein said ultraviolet disinfection source comprises a lamp type GPH127T5L as manufactured by First Light Technologies, Inc., or functional equivalent.

8. The water disinfection device of claim 7, wherein the distance between the surface of said lamp and the interior of said durable container is less than 7.5 centimeters at any point except the opening.

9. The water disinfection device of claim 7, wherein said ultraviolet source is above the opening of the durable container by an amount not exceeding ⅜ inch, for the purpose of disinfecting the opening itself as well as the surrounding surfaces.

10. The water disinfection device of claim 1, wherein the interior of said durable container has a reflective means.

11. The water disinfection device of claim 6, wherein the interior of said dome has a reflective means.

* * * * *